(12) United States Patent
Weitzel et al.

(10) Patent No.: US 9,884,157 B2
(45) Date of Patent: Feb. 6, 2018

(54) INHALATION DEVICE, CONTROL METHOD AND COMPUTER PROGRAM

(71) Applicant: MicroDose Therapeutx, Inc., Ewing, NJ (US)

(72) Inventors: Douglas Weitzel, Hamilton, NJ (US); Anand V. Gumaste, West Windsor, NJ (US); Philip Chan, Hightstown, NJ (US)

(73) Assignee: MicroDose Therapeutx, Inc., Ewing, NJ (US)

( * ) Notice: Subject to any disclaimer, the term of this patent is extended or adjusted under 35 U.S.C. 154(b) by 248 days.

(21) Appl. No.: 14/196,414

(22) Filed: Mar. 4, 2014

(65) Prior Publication Data
US 2014/0261414 A1    Sep. 18, 2014

Related U.S. Application Data

(60) Provisional application No. 61/792,607, filed on Mar. 15, 2013, provisional application No. 61/910,179, filed on Nov. 29, 2013.

(51) Int. Cl.
*A61M 15/00* (2006.01)
*G01F 1/68* (2006.01)
(Continued)

(52) U.S. Cl.
CPC ........ *A61M 15/002* (2014.02); *A61M 15/001* (2014.02); *A61M 15/0045* (2013.01);
(Continued)

(58) Field of Classification Search
CPC .... A61M 2202/064; A61M 2202/0007; A61M 15/001; A61M 15/0045; A61M 15/0051; A61M 15/0085; A61M 2016/0036
See application file for complete search history.

(56) References Cited

U.S. PATENT DOCUMENTS 3,962,917 A * 6/1976 Terada ................. A61B 5/0816
600/537
4,363,238 A    12/1982 Willam ......................... 73/204
(Continued)

FOREIGN PATENT DOCUMENTS

CN    1753700 A    3/2006
CN    1925887 A    3/2007
(Continued)

OTHER PUBLICATIONS

International Search Report and Written Opinion issued in corresponding PCT Patent Appln. Serial No. PCT/US2014/025077 dated Jun. 16, 2014 (16 pages).
(Continued)

*Primary Examiner* — Peter S Vasat
(74) *Attorney, Agent, or Firm* — Condo Roccia Koptiw LLP

(57) ABSTRACT

The invention provides an inhalation device using an electrically driven vibratory element for releasing a drug dose into a flow channel, and a controller for activating/deactivating the vibratory element. A sensor arrangement is able to differentiate between inhalation flow and exhalation flow through the flow channel, to assist in forming a model of the breathing pattern of the user. The device can detect reliably inhalation flow patterns from patients of all ages.

20 Claims, 11 Drawing Sheets

(51) Int. Cl.
*G01F 11/00* (2006.01)
*A61M 16/00* (2006.01)

(52) U.S. Cl.
CPC .... *A61M 15/0051* (2014.02); *A61M 15/0085* (2013.01); *G01F 1/68* (2013.01); *G01F 11/003* (2013.01); *A61M 2016/0021* (2013.01); *A61M 2016/0036* (2013.01); *A61M 2202/064* (2013.01); *A61M 2205/3317* (2013.01); *A61M 2205/3368* (2013.01); *A61M 2205/3653* (2013.01); *A61M 2205/50* (2013.01)

(56) References Cited

U.S. PATENT DOCUMENTS

| | | | |
|---|---|---|---|
| 4,465,234 A | 8/1984 | Maehara et al. | |
| 5,487,378 A | 1/1996 | Robertson et al. | 128/200.16 |
| 6,026,809 A | 2/2000 | Abrams et al. | 128/203.15 |
| 6,990,975 B1 | 1/2006 | Jones et al. | |
| 7,021,560 B2 | 4/2006 | Gray et al. | |
| 2001/0003922 A1 | 6/2001 | Engel | 73/204.11 |
| 2002/0046750 A1 | 4/2002 | Gonda et al. | 128/200.14 |
| 2003/0136402 A1 | 7/2003 | Jiang et al. | |
| 2003/0172927 A1* | 9/2003 | Young | A61M 15/0045 128/203.15 |
| 2004/0050385 A1* | 3/2004 | Bonney | A61M 15/0065 128/203.15 |
| 2004/0187864 A1 | 9/2004 | Adams | |
| 2005/0183725 A1* | 8/2005 | Gumaste | A61M 15/0085 128/203.15 |
| 2005/0268911 A1* | 12/2005 | Cross | A61M 15/0045 128/204.17 |
| 2007/0137645 A1 | 6/2007 | Eason et al. | |
| 2009/0133490 A1 | 5/2009 | Zschernack et al. | 73/204.27 |
| 2011/0162642 A1 | 7/2011 | Akouka et al. | |
| 2012/0291779 A1 | 11/2012 | Haartsen et al. | |
| 2013/0220321 A1 | 8/2013 | Eason et al. | |

FOREIGN PATENT DOCUMENTS

| | | | |
|---|---|---|---|
| CN | 101564569 A | 10/2009 | |
| CN | 102665807 A | 9/2012 | |
| CN | 102762246 A | 10/2012 | |
| EP | 0 024 327 | 3/1981 | A61B 5/08 |
| JP | 2006-514573 | 5/2006 | |
| WO | WO 1989/06147 A1 | 7/1989 | |
| WO | WO 92/11050 | 7/1992 | A61M 15/00 |
| WO | WO 97/26934 | 7/1997 | A61M 15/00 |
| WO | WO 98/48873 | 11/1998 | A61M 11/00 |
| WO | WO 2001/32246 A1 | 5/2001 | |
| WO | WO 2005-030306 A2 | 4/2005 | |
| WO | WO 2005-120614 A1 | 12/2005 | |
| WO | WO 2011/085022 A1 | 7/2011 | |
| WO | WO 2011/089490 A1 | 7/2011 | |
| WO | WO 2011/161060 | 12/2011 | A61M 16/00 |

OTHER PUBLICATIONS

International Preliminary Report on Patentability issued in application No. PCT/US2014/025077, dated Sep. 24, 2015 (10 pgs).
U.S. Sensor Corp., "Thermistor Terminology", Available on internet http://www.ussensor.com/technical-info/thermistor-terminology , Aug. 14, 2012, 2 pages.

* cited by examiner

INHALATION DEVICE, CONTROL METHOD AND COMPUTER PROGRAM

This application claims the benefit of priority from U.S. 61/792,607, filed 15 Mar. 2013 and U.S. 61/910,179, filed 29 Nov. 2013.

This invention relates to inhalation devices, particularly but not exclusively for inhalation of a dry power medication.

A known type of dry powder medication inhalation device comprises a blister pack having a set of blisters which each contain a dose of powdered medication. The blister pack is advanced in "dose advance" steps.

Currently available inhalation devices lack the ability to ensure that a released dose is inhaled by the patient as desired: more particularly, currently available devices fail to appropriately couple dose advance and delivery mechanisms to relevant trigger signals.

What is needed therefore is an improved drug delivery device whereby such device delivers an appropriate dosage of a therapeutic drug in response to a trigger. Devices that respond to triggers such as inhalation, for example inhalation as detected through a facemask connected to an inhaler, are particularly desired. Desirably, such devices minimize or diminish the false release of the therapeutic drug.

The invention is defined by the claims.

According to the invention, there is provided an inhalation device for delivering powdered medication from a container through a flow channel to a patient, said inhalation device comprising:

an electrically driven vibratory element;

a controller for activating/deactivating the vibratory element; and a sensor arrangement system comprising a first sensor physically arranged to face inhalation air to generate an inhalation flow signal and a second sensor physically arranged to face exhalation air to generate an exhalation flow signal, wherein the controller is adapted to process the inhalation flow signal and exhalation flow signal to generate a trigger signal for controlling the timing of operation of the vibratory element.

By differentiating between inhalation and exhalation air, it is possible to construct a function which represents more accurately the breathing pattern of the user. This function can then be used to provide the trigger points for the control of the vibratory element. The vibratory element for example comprises a piezoelectric vibrator.

The sensor system used allows the inhaler to detect the very low flow rate which occurs at the beginning of a breath, and controls the drug delivery when the patient is spontaneously breathing in a tidal manner. The inhalation detection system can be adapted for use with patients ranging from newborns to adults.

The container of the device may comprise a blister pack, and the device may further comprise a blister advance mechanism. This blister advance mechanism can then also be controlled based on the trigger signal.

The first sensor and the second sensor may each comprise self-heated thermistor sensors. These detect a level of cooling, which is dependent on the air flow past the sensor.

The first sensor and the second sensor are preferably biased with constant current so as to maintain a temperature higher than ambient (in particular the highest ambient temperature specified as being within the operating temperature range for the device). In this way, a degree of cooling can always be detected. The thermistors may for example be biased with a constant current so as to maintain a temperature higher than about 50° C.

The device preferably has a circuit or processor which combines signals from the first and second thermistors and amplifies those signals to generate a signal that indicates direction of air flow.

This direction signal can for example be derived from difference between the inhalation flow sensor signal and the exhalation flow sensor signal. This difference can be amplified to provide the direction signal. The evolution of the air flow direction provides timing information concerning the breathing flow rate of the user, which can be used to construct a breathing flow rate function.

The device can further comprise a circuit or processor for processing a signal from the first thermistor to generate a flow signal proportional to air flow. This flow signal can be derived from a combination of the inhalation air flow signal and the derivative with respect to time of the inhalation air flow signal. The derivative signal can be given a stronger weighting before the two signals are combined.

The device can further comprise a circuit or processor for decoupling a signal from the inhalation thermistor to generate a signal indicating an operating temperature.

The controller can further comprise a circuit or processor for processing the flow signal and direction signals to generate respective baseline signals and to provide baseline-corrected flow signal and direction signals.

This enables a baseline tracking and compensation function to be carried out. The baseline tracking can be operated with a first time constant so that the baseline is defined as closely following a function being tracked, while an inhalation is awaited. A slower second time constant can be used when an inhalation is detected, so that the baseline tracks the flow and direction signals more slowly while an inhalation breath takes place. The close baseline tracking can then resume after the inhalation and exhalation.

The controller is preferably adapted to process the baseline-corrected flow signal and direction signals to generate a flow function, and to generate the trigger signal from the flow function. In this way, the trigger signal is obtained from a flow function, which has been derived following baseline tracking, so that a change in the flow function can reliably and rapidly detect an inhalation breath.

The invention also provides a method of controlling an inhalation device for delivering powdered medication from a container through a flow channel to a patient, the method comprising:

using a first sensor facing inhalation air to generate an inhalation flow signal;

using a second sensor facing exhalation air to generate an exhalation flow signal, processing the inhalation flow signal and exhalation flow signal to generate a trigger signal for controlling the timing of operation of an electrically driven vibratory element for releasing the medication into the flow channel.

This method makes use of measurements of inhalation and exhalation air flow in order to provide a reconstruction of the air flow in the device air channel. This is then used to control the timing of dose delivery.

Generating an inhalation flow signal and generating an exhalation flow signal can each comprise measuring a degree of cooling of a thermistor sensor, and the method comprises biasing the thermistors with a constant current so as to maintain a temperature higher than ambient.

The first and second thermistor signals can be combined to generate a direction signal that indicates direction of air flow, and the signal from the first sensor can be processed to generate a flow signal proportional to air flow. The flow signal can also be used to derive a signal indicating an operating temperature.

The method can further comprise processing the direction signal and the flow signal to generate respective baseline signals, and adapting the direction signal and the flow signal to provide baseline-corrected direction and flow signals. This baseline correction enables only significant desired changes in the signals to be detected for example reducing false triggers.

The method can further comprise:

obtaining a derivative signal which is the derivative with respect to time of the baseline-corrected direction signal; and creating a polynomial function which represents the air flow through the flow channel which has a term comprising a multiple of the baseline-corrected direction signal, a term comprising a multiple of the baseline-corrected flow signal, and a term comprising a multiple of the derivative signal.

This polynomial function is a three-term polynomial for representing the flow in the air channel.

The trigger signal is then derived from the polynomial function. The trigger signal is for initiating a dose advance function when a first valid inhalation has been detected following wake-up of the inhaler, or activating the vibratory element to deliver a burst of medication powder when the trigger follows a dose advance and throughout a dosing session.

The invention also provides computer program comprising computer program code adapted to perform the steps of the method of the invention when said program is run on a computer.

An example of the invention will now be described in detail with reference to the accompanying drawings, in which.

The invention provides an inhalation device using an electrically driven vibratory element for releasing a drug dose, typically a powdered drug dose, into a flow channel, and a controller for activating/deactivating the vibratory element. A sensor arrangement is able to differentiate between inhalation flow and exhalation flow through the flow channel, and to assist in forming a model of the breathing pattern of the user. The present invention can include software comprising a breathing validation algorithm enabling appropriate mechanisms that trigger the release of a drug, upon detection of a valid breath. The present invention in this way can reject unwanted triggers and discriminate against false input such as irrelevant movement of the device.

The inhalation device can for example use a blister pack, in which a blister is positioned at a release location and is then opened, and the contents are released. This release of the contents is for example caused partly by the air flow, induced by inhalation of the user, over the blister, but also a piezoelectric vibrating arrangement is used to assist in the emptying of the blister content into the air flow channel leading to the drug delivery orifice of the device. The piezoelectric actuation corresponds to a "dosing burst" during which the drug is to be inhaled.

The timing of the operation of the dose advance mechanism and the piezoelectric vibrating arrangement is critical in ensuring that the released dose is inhaled by the patient as desired, and to control the dose delivered to the patient.

In particular, the device should deliver bursts of powdered drug each time the patient inhales through a face mask connected to the inhaler, and false release of drug should be avoided.

This invention thus relates to the control of the timing of the dose delivery functions performed by the inhalation device. It relates in particular to the reliable detection of the timing of each inhalation breath of the user.

Figure 1:
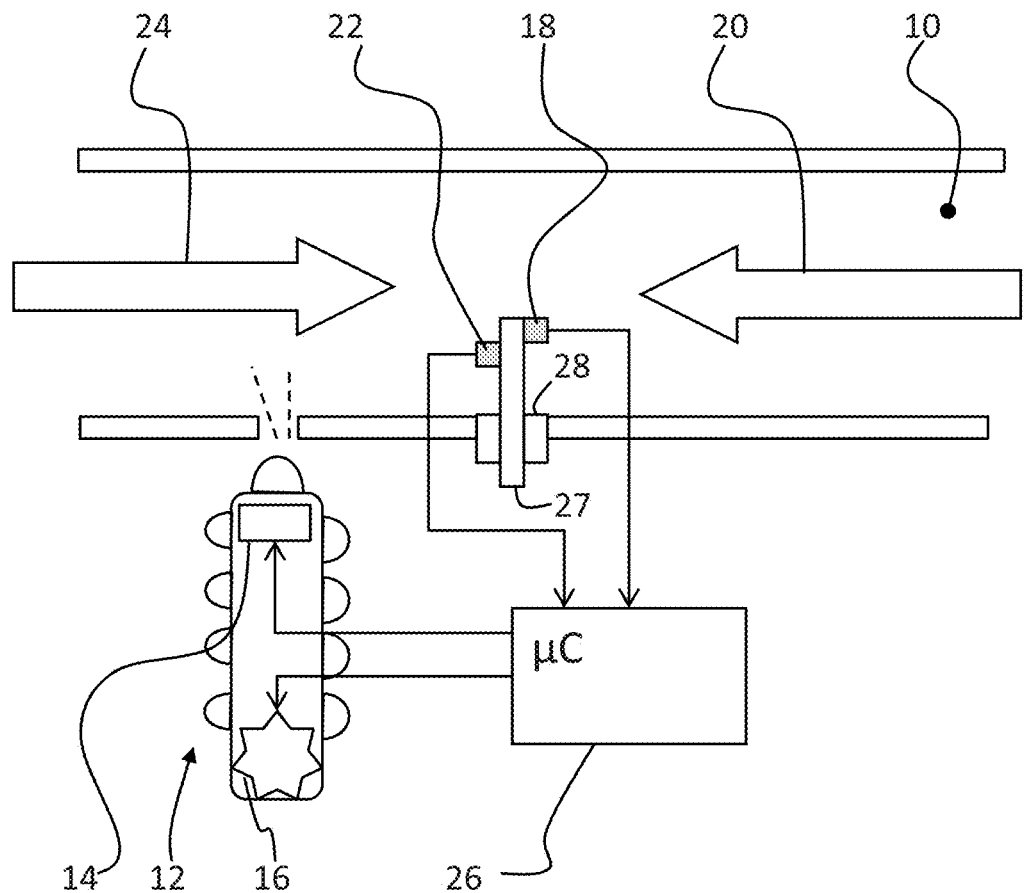
FIG. 1 shows an example of the sensor arrangement used in the device of the invention.

FIG. 1 shows an example of the sensor arrangement used in the device of the invention.

A flow channel 10 is shown, which is present between an air intake port of the inhalation device and an opening at which medication is delivered to the patient. The patient can for example wear a face mask. The air flow along the passageway 10 is passive, namely caused by the inhalation and exhalation of the patient. At a point along the passageway 10, a powder drug is introduced into the passageway, for inhalation by the patient. For this purpose, a blister pack of drug delivery capsules is shown in simplified schematic form as 12, and a piezoelectric vibrator 14 is used to assist in the emptying of an opened blister into flow channel. The operation time of the vibrator is termed a "dosing burst". The blister pack is advanced by a drive mechanism, shown schematically as the cog 16. The operation of the drive mechanism is termed a "dosing advance".

Descriptions of piezoelectric vibrators, drive mechanisms and drug capsules suitable for use with this invention are known to those skilled in the art. The drug is typically released from the blister capsule into a dosing chamber from which it is entrained into the air flow in the passageway 10.

A sensor arrangement is provided, comprising an inhalation flow sensor 18 in the form of a thermistor which faces the inhalation air flow 20 and an exhalation flow sensor 22 in the form of a thermistor which faces the exhalation air flow 24.

A controller 26 is provided for activating and deactivating the vibratory element 14, and also controlling the drive mechanism 16. The controller uses the flow sensor signals to differentiate between inhalation flow and exhalation flow through the flow channel 10. As shown, the controller receives the sensor signals, and provides control signals to the drive mechanism 16 and vibrator element 14.

Although shown as a separate unit, the controller can be integrated onto a printed circuit board 27 on which the sensors 18, 22 are mounted, which is sealed into the air channel wall by a gasket 28.

The location at which the drug is delivered into the air flow channel may be before or after the location of the sensing arrangement.

Figure 2:
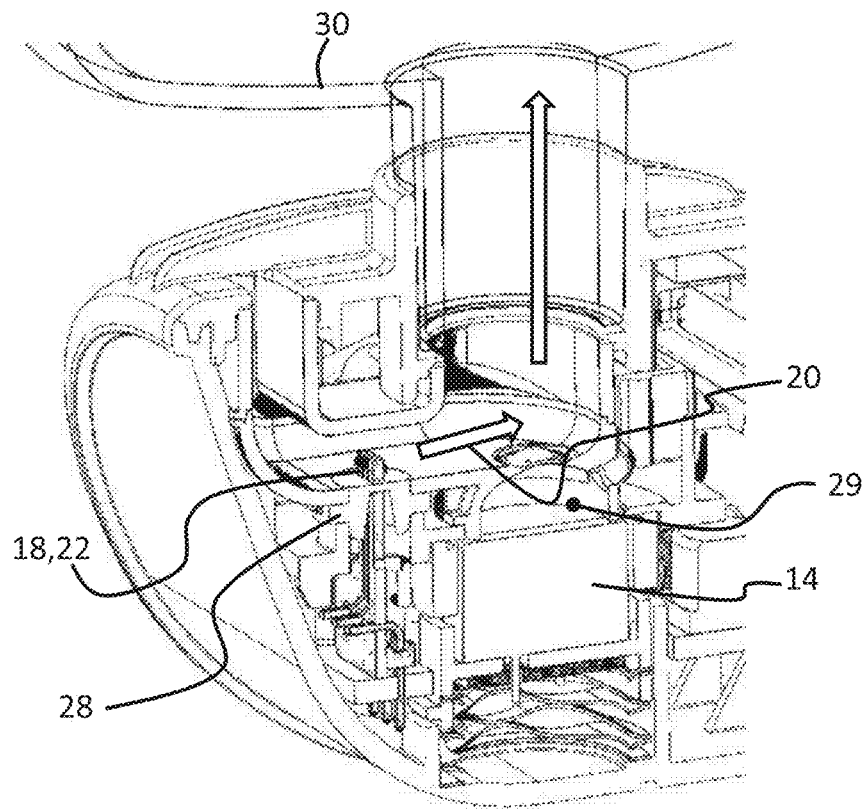
FIG. 2 shows how the sensors fit into the flow channel arrangement of an inhalation device with a mask.

FIG. 2 shows the sensor arrangement mounted within an inhaler device, in cross section. The inhalation flow is shown as arrow 20, which leads to a face mask 30. The sensor head 18,22, the piezoelectric vibrator 14 and the gasket 28 are shown, as well as the dosing chamber 29.

The sensors provide an inhalation detection system. Generally, this system is designed to satisfy the following general requirements and design guidelines:

Enable triggering of dose advance and dosing bursts when the inhalation air flow through the inhaler's flow channel exceeds a minimum flow rate. This minimum flow rate is typically 0.2-5 LPM (liters per minute), preferably greater than 0.5 LPM, but this target may change according to the patient population to be treated. In some applications, it may also be desirable to place an upper limit on the flow rate within which the triggering must occur.

Be able to operate with flow rates and tidal volumes encountered with pediatric and adult breathing.

Operation independent of the flow channel's flow resistance.

Operate in typical ambient conditions found in a hospital or home.

The cost of the inhalation detection subsystem components must be low enough to allow the unit cost of the fully packaged commercial product.

Sensor(s) should not require precise placement with respect to facial features.

The sensor(s) used to detect air flow must not impede air flow or drug delivery.

Must not trigger the inhaler functions when exhalation air flow is present in the inhaler's flow channel.

Must not trigger during routine handling of the inhaler prior to dosing.

Discrimination of air flow direction is required, but measurement of exhalation flow rate is not required.

To provide the air flow sensing, two small thermistors 18,22 (0402 surface mount technology packages) are placed inside the inhaler flow channel 10. As mentioned above, the sensors are physically arranged so that one faces inhalation air and the other faces exhalation air. The sensor system is selected and designed to be inherently sensitive to low flow rates due to the very low thermal mass of the thermistor sensors and a relatively small cross-sectional area of the flow channel to concentrate the air flow in the region of the sensor, as can be seen in FIG. 2. Both thermistors are biased with constant current so that they maintain a higher temperature than ambient (typically 50° C. to 55° C. to guarantee operation at least 10° C. above the typical highest specified operating temperature of 40° C.).

Air flow temporarily cools the thermistors, with the dominant cooling effect occurring on whichever thermistor faces the instantaneous direction of air flow, and the resulting change in resistance is detected as change in voltage across thermistors. Because of the constant current bias, the thermistor terminal voltage increases due to air flow, and the voltage increase is proportional to the air flow rate.

The thermistors are thus effectively configured as hot wire anemometers.

The thermistor on the inhalation side of the sensor is placed near the tip to increase the cooling effect, whereas the thermistor on the exhalation side is offset to partially decouple the thermistor from the heat generated by the inhalation sensor. This is shown in FIG. 1.

Signals are generated by op-amp circuits included in the inhaler's main circuit board:

(i) Both thermistor signals are combined and amplified to generate a signal that indicates direction of air flow (denoted as the "DIR" signal).

$$DIR=10*(\text{inhalation voltage}-\text{exhalation voltage})$$

(ii) The inhalation thermistor signal is amplified to generate an inhalation voltage signal (called "INHALE_A" in the figures below). A time derivative of this signal is formed and combined with the original signal to derive a flow signal proportional to the air flow rate ("FLOW"):

$$FLOW=(50*\text{derivative of inhalation voltage})+\text{inhalation voltage}$$

(iii) The inhalation thermistor signal is DC-coupled to generate a signal indicating the operating temperature (denoted as "TEMP").

Factory calibration establishes a baseline TEMP signal level corresponding to a known ambient temperature of 23° C.±2° C.

Figure 3:
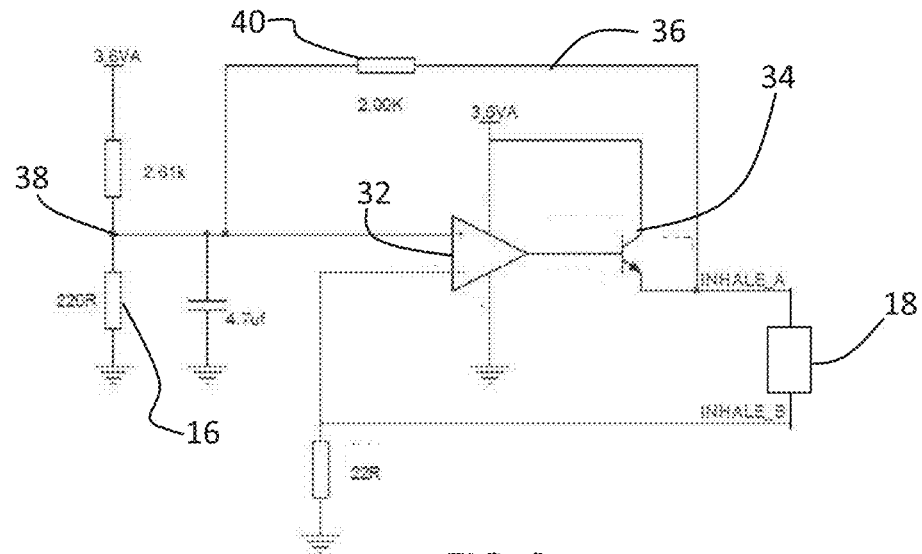
FIG. 3 shows the circuit for generating an inhale signal. An analogous circuit is used to generate an exhale signal.

FIG. 3 shows the circuit for generating the inhale signal INHALE_A, and which provides thermistor biasing. An analogous circuit is used to generate an exhale signal.

A current is driven through the inhalation thermistor 18 from the high voltage rail (3.6VA). The thermistor has two terminals, INHALE_A and INHALE_B. The INHALE_A terminal is used as the output terminal which is processed by the other circuitry.

A low resistance of 100Ω of the thermistor 18 is chosen so that it can be self-heated by a small injection of current. The thermistors are NTC (negative temperature coefficient) in which the resistance goes down as temperature increases. When a current is applied to the thermistor, it heats up quickly due to its small size and NTC properties and establishes thermal equilibrium with its surroundings quickly. The self-heated NTC thermistor will always be at a higher temperature than ambient.

In one example of design, the thermistors are heated to a temperature that is greater than the ambient temperature by approximately 5-20 degrees, preferably 10-18 degrees, and most preferably approximately 15 degrees. In certain embodiments, the thermistors have a constant temperature of about 50° C. so that they will always be cooled due to either inhalation air or exhalation air that is always less than approximately 40° C.

An input potential divider sets the DC operating point of the circuit.

The circuit is comprised of an operational amplifier 32 in a constant current source topology, namely with a transistor 34 at the output.

A feedforward resistor 40 changes the bias point slightly depending on the voltage at the output INHALE_A. if the output voltage is higher than the initial value at the non-inverting input of the operational amplifier 32, then the output voltage pulls up the non-inverting input voltage.

When there is a detected air flow, the thermistor resistance changes rapidly and results in changes in all node voltages.

There is a positive feedback effect and a negative feedback effect, which together have the effect that at the output INHALE_A, the voltage starts to propagate from the output to the non-inverting input of the amplifier, then back to the output again, until the circuit stabilizes.

When the thermistor 18 is cooled by air flow, its resistance increases. This in turn increases the voltage at INHALE_A due to the constant current source topology. This voltage is coupled by the resistor 40 to the non-inverting input. This in turn raises the output voltage at INHALE_A. This is a form of positive feedback loop.

Due to the higher output voltage at the output INHALE_A, the thermistor receives a larger bias voltage and this results in a larger current to flow. This in turn results in larger power dissipation and eventually increases the thermistor temperature. Due, to this heating, the thermistor resistance reduces, and therefore INHALE_A voltage drops. This completes a negative feedback loop.

The two feedback mechanisms work together to stabilize temperature and to control the response characteristics of the circuit.

This hardware control algorithm over-compensates for the reduction in temperature to speed up the temperature recovery due to transient cooling of thermistor due to airflow.

The exhale thermistor 22 is placed in an identical circuit to that shown in FIG. 3, to generate an exhale signal EXHALE_A as its output. The exhale thermistor has two terminals EXHALE_A and EXHALE_B.

Figure 4:
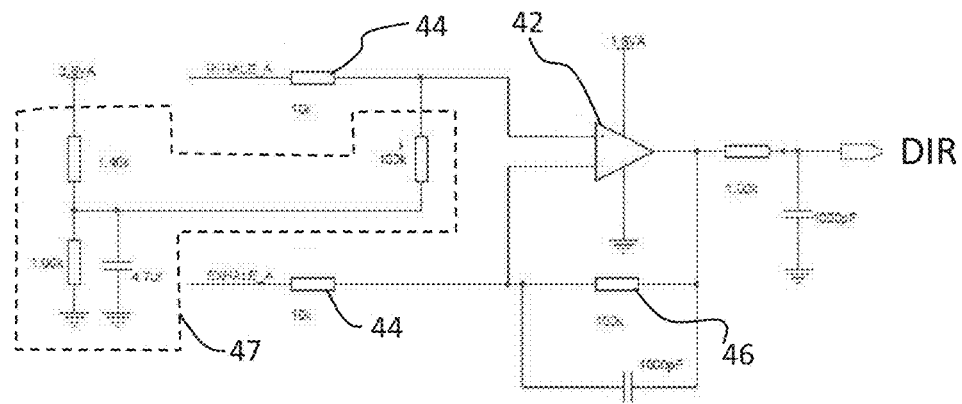
FIG. 4 shows a circuit for generating a flow direction signal from the inhale and exhale signals.

FIG. 4 shows a flow direction amplifier circuit, in the form of an op-amp difference amplifier that subtracts the exhalation signal from the inhalation signal, so that direction of flow can be fed back to the controller.

The circuit comprises an operational amplifier 42 which receives the inhale signal to the non-inverting input and the exhale signal to the inverting input. A gain of 10 is provided by the input resistors 44 of 10 kΩ and the feedback resistor 46 of 100 kΩ. This implements the flow direction function DIR=10*(inhalation voltage−exhalation voltage).

A low pass filter is shown at the output of the circuit.

The input of the circuit also has a biasing arrangement 47 to center the output at a desired level, such as 1.5V.

The difference amplifier topology of FIG. 4 returns the difference between the inhalation flow and the exhalation flow. In the event of strong flow, both the inhalation sensor and the exhalation sensor experience a cooling effect due to turbulent flow near the sensors. However, the sensor facing the airflow will experience the most cooling effect and produce the largest amount of voltage output. Therefore, a difference of the inhalation sensor output and the exhalation sensor output represents direction of flow.

Figure 5:
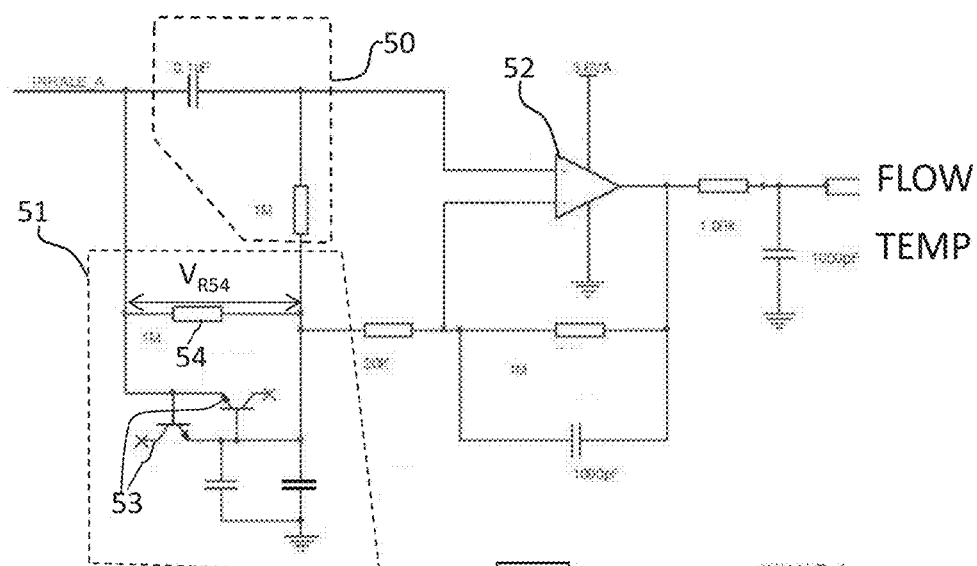
FIG. 5 shows a circuit for generating a temperature measurement from the inhale signal.

FIG. 5 shows a flow amplifier circuit for generating the FLOW signal from the amplified inhale signal INHALE_A as well as a temperature signal TEMP. These FLOW and TEMP signals together can be considered to be an "Inhale channel".

This flow amplifier circuit returns the temperature of the flow sensor TEMP as a DC magnitude with a gain of 1 and the flow amplitude as a rising edge amplitude (AC) signal with a gain of 50.

An RC circuit 50 provides differentiation of the INHALE_A signal. This differentiation is implemented by the AC coupling provided by the capacitor, with a time constant in this example of 1 s.

A DC bridge 51 derives the DC component of the INHALE_A signal. The DC bridge comprises a transistor pair 53 and input resistor 54. When the voltage difference across resistor is large, the transistor pair 53 clamps the voltage across the resistor 54. The resistor thus functions as a voltage controlled resistance. When the voltage $V_{R54}$ across the resistor 54 is large, the resistance decreases to zero Ohms due to the transistor clamp. When the voltage is small, resistance becomes 1 MOhm.

The circuit comprises an operational amplifier 52 with negative feedback amplification, and which amplifies the differentiated (AC coupled) INHALE_A signal with a gain of 50 and combines this with the DC path signal from the inhalation sensor.

This circuit provides dual behavior: when DC difference between INHALE_A and the output is large, the circuit cancels any difference. At the same time, it allows the AC amplitude to be amplified 50 times.

The DC bridge circuit 51 creates a virtual ground at an elevated DC voltage which is equal to the DC component of INHALE_A. It does so without large time constant that would lead to time lag induced inaccuracy. After power up, circuit 51 stabilizes in less than 0.1 second, so that hardware accuracy is ensured within 0.5 second of device warm-up time. After this, the circuit becomes a virtual ground.

The amplifier 52 sums the output of 51 and 50 times the output of circuit 50 and presents its output at to the circuit output.

The AC output of the circuit is the FLOW value outlined above:

FLOW=(50*derivative of inhalation voltage)+inhalation voltage

The DC output of the circuit is the temperature value TEMP. As the ambient temperature changes, the terminal voltage INHALE_A of the heated thermistor, biased with a constant current, changes. The thermistor voltage is thus related to the ambient temperature of air near the thermistor. The DC voltage is fed back to the controller by means of the TEMP signal so that gain drift due to the temperature of the thermistor can be corrected.

In this way, the function FLOW function is implemented: Thus, the FLOW signal combines the inhale sensor signal DC and its amplified time derivative.

The outputs of the circuits of FIGS. 4 and 5 are provided to an analogue to digital converter, for further processing in the digital domain. They can be multiplexed together for supply to a digital signal processor (DSP).

Figure 6:
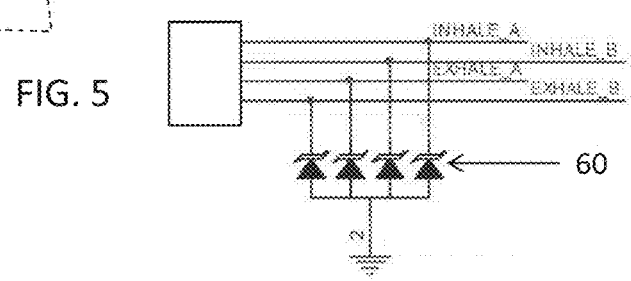
FIG. 6 shows that the inhale and exhale thermistors are protected with ESD diodes.

FIG. 6 shows that the inhalation and exhalation sensor terminal are protected by ESD Zener diodes 60.

Figure 7:
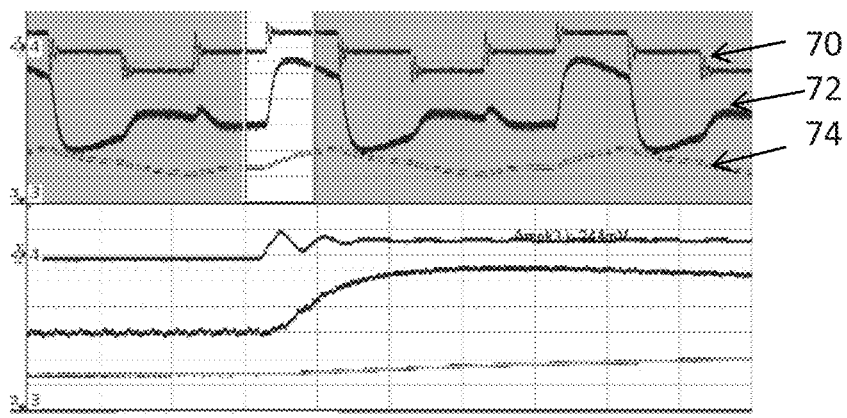
FIG. 7 is a timing diagram showing the flow and direction signals at room temperature.

FIG. 7 shows the sensor signals with a 5 LPM air flow step input at room temperature. Plot 70 shows the actual airflow signal from a pneumotachometer. Plot 72 shows the FLOW signal and plot 74 shows the DIR (direction) signal.

The bottom part of the image is an enlarged version of part of the top part of the image.

Figure 8:
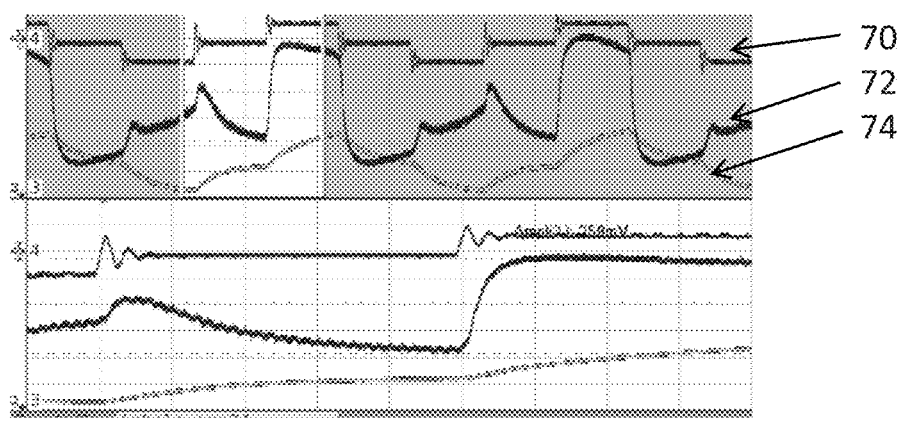
FIG. 8 is a timing diagram showing the flow and direction signals at 3 degrees.

FIG. 8 shows the same set of signals with the same 5 LPM air flow step input but at 3° C. Note the larger FLOW and DIR signal amplitudes due to a stronger cooling effect from cold ambient air on the self-heated thermistors.

Figure 9:
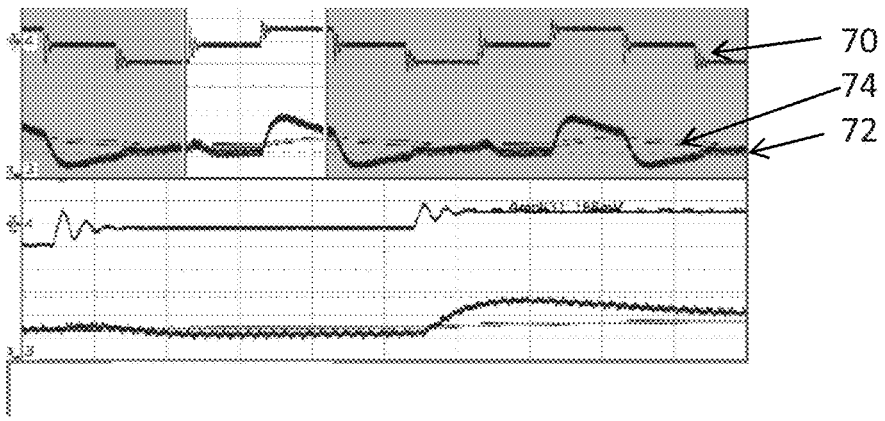
FIG. 9 is a timing diagram showing the flow and direction signals at 40 degrees.

FIG. 9 shows the same set of signals with the same 5 LPM air flow step input but at 40° C. Note the smaller FLOW and DIR signal amplitudes resulting from a reduced cooling effect from warm ambient against the warm thermistors.

Figure 10:
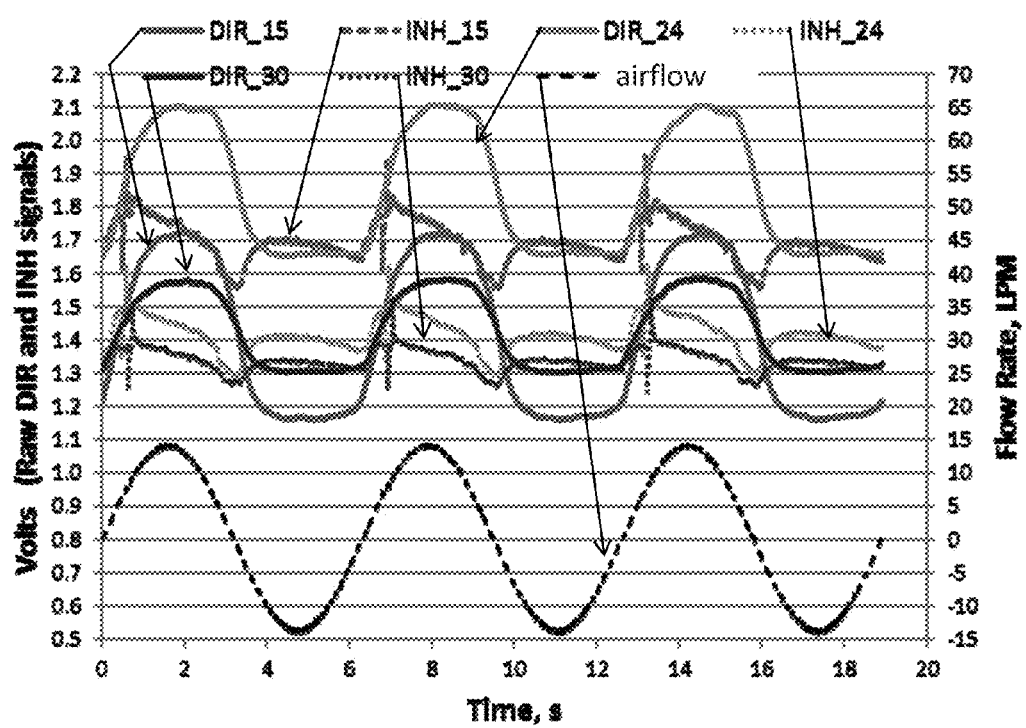
FIG. 10 is a timing diagram showing the flow and direction signals for one inhaler at various temperatures.

FIG. 10 shows typical DIR and Inhalation channel signals captured at different operating temperatures (15, 24 and 30 degrees) with the same inhaler unit. The three inhalation channel signals (i.e. the AC signal FLOW+TEMP) are labeled INH_15, INH_24 and INH_30, and the three DIR signals are labeled DIR_15, DIR_24 and DIR_30. Note the shifts in both DC offset and signal amplitude with temperature. The signal "airflow" shows the actual airflow.

As mentioned above, the output of the overall detection system is a software trigger that signals the inhaler system software to execute one of two different actions:

(i) Initiate a blister strip dose advance when the trigger is the first valid inhalation detected following wake-up of the inhaler; or (ii) Excite the piezoelectric transducer for delivering a burst of powder when the trigger follows the dose advance and throughout the dosing session.

Inhalation detection system errors can be grouped into two main categories, listed below. Design verification testing during development is used to demonstrate that the occurrence of these types of errors is minimized by using a range of simulated breathing test cases.

(i) Triggering occurs at the wrong time; that is, when presented with conditions other than inhalation within the specified flow sensor range such as exhalation, excessive inhaler motion, or trigger flow sensor voltage too high or low.

(ii) Triggering does not occur when valid breathing is present.

Potential risks of triggering at the wrong time include:

(i) Possibility of ejecting powdered drug out of the flow channel inlet with exhalation.

(ii) Ineffective dosing resulting from powder settling in the flow channel or face mask that does not get properly inhaled.

(iii) Exposing the dose (in the event of an unintended dose advance) before intending to complete the dosing session, resulting in a wasted dose through purging.

Potential risks of not triggering with valid breathing include:

(i) Unable to dose at all.

(ii) Requiring more inhalations (more time) to complete the full dose.

(iii) Being unable to complete the dose before a dose timeout occurs, resulting in a wasted dose through purging.

(iv) Drug powder being ejected at a point in time where it will not be properly inhaled by the patient.

The inhalation detection algorithm utilizes a three-tem polynomial to essentially "reconstruct" the actual flow rate sensed by the dual thermistor sensor. The inputs to the algorithm are the flow direction (DIR) and flow amplitude/operating temperature (FLOW and TEMP) signals described above.

The algorithm is designed to not necessarily 'faithfully reproduce' the input flow signal, but rather:

To have higher sensitivity at low flow levels so that inhalation breath can be detected early in the breath cycle;

To minimize the response time to a positive going inhalation transition;

To have variable gain so that low flows are amplified more than high flows. Accuracy of the flow rate estimation is not needed at higher flow rates, since the initial inhalation timing is of principal interest. To minimize the response time to a positive-going inhalation transition;

To provide ambient temperature compensation; and

To simplify the algorithm by de-emphasizing the reproduction of the exhalation portion of the flow (this reduces algorithm complexity by minimizing the number of terms in the polynomial).

Gain compensation mechanisms are used to improve the reliability of operation. A thermistor under bias with a high DC voltage has a lower gain. Therefore, this operation should be compensated with a higher gain. On the contrary, a thermistor under bias with a low DC voltage output has a higher gain. Therefore, this operation should be compensated with a lower gain. Thus, gain compensation depending on the operating point is desired.

An intrinsic gain value can be defined, for example:

$$\text{IntrinsicGain} = 0.2731 * (\text{FLOW}_{DC23C} - 3273) + 515.2$$

In this relation, $\text{FLOW}_{DC23C}$ is a calibration value of the FLOW signal DC amplitude at a 23° C. calibration condition at the factory.

Overall, the following equation is the output polynomial equation representing the flow in the channel:

$$\text{Flow}(t) = (A*\text{DIR}) + (B*d\text{DIR}/dt) + (C*\text{FLOW})$$

When temperature gain and intrinsic gain are applied to this function, the following expressions for the polynomial terms is derived, which represents the flow output under all conditions:

$$A = \text{Gain1} * \text{TempGain} * \text{IntrinsicGain}$$

$$B = \text{Gain2} * \text{TempGain} * \text{IntrinsicGain}$$

$$C = *\text{Gain3} * \text{TempGain} * \text{IntrinsicGain}$$

The value TempGain is a temperature gain compensation factor, and the value IntrinsicGain is the intrinsic, factory-set gain compensation factor defined above.

The temperature gain compensation factor TempGain is defined as:

$$\text{TempGain} = \text{Gain} * (\text{FLOW}_{DCAV} - \text{FLOW}_{DC23C})$$

wherein

Gain is the gain transfer function of the sensor, $\text{FLOW}_{DCAV}$ is the average of the present FLOW signal DC amplitude. Note that this average is obtained by digital signal processing.

By way of example, the constant gain values can be:

Gain1=4

Gain2=16

Gain3=4

As defined above:

DIR=the AC part of the output of the flow direction amplifier of FIG. 4;

dDIR/dt=the first derivative of the DIR signal with respect to time;

FLOW=the AC part of the output of the flow amplifier of FIG. 5.

As mentioned above, ambient temperature can be derived from the DC part of the inhalation channel signal at the output of the circuit of FIG. 5. The DC voltage component correlates to the ambient temperature indirectly. Given the fact that the inhalation sensor is actually heated to about 50° C., its temperature will not be the ambient temperature. However, at a given ambient temperature, the inhalation channel thermistor will be heated to a corresponding unique value. Based on characterization data, the ambient temperature can be inferred from the thermistor temperature.

In order to provide temperature compensation, devices have been evaluated over an extended temperature range of 5° C. to 40° C.

Sensor voltage outputs have been measured using standard flow rates over the extended temperature range. From the data, a compensation transfer function, called "Relative Gain to be Applied" has been developed. The compensation transfer function is approximated by a two-segment piecewise linear function centered at 23° C., shown in FIG. 11 (not to scale). This is the relative gain value to be applied to the uncompensated sensor output.

Above 23° C., the sensor is less sensitive to airflow (lower gain), so a higher compensating gain is applied. Below 23° C., the sensor is more sensitive to airflow (higher gain), so a lower compensating gain is applied. The goal of the temperature compensation is to maintain a relatively constant gain throughout the entire operating temperature range. In this way, the output for the signal processing algorithm for a given breath remains constant over a given operating temperature range.

Figure 11:
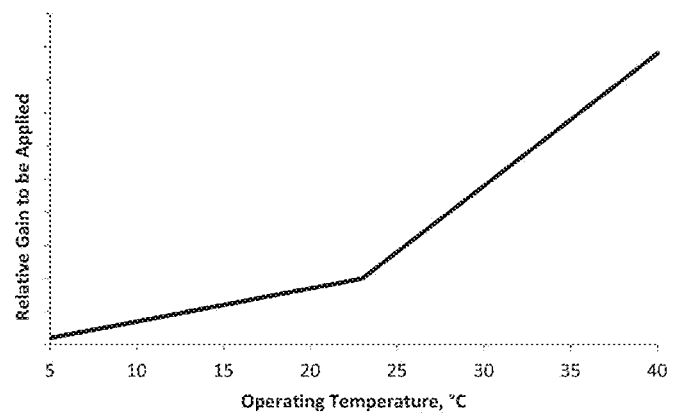
FIG. 11 shows a temperature compensation transfer function which can be used.

FIG. 11 shows that the value "Relative Gain to be Applied" is temperature-dependent. The transfer function of the value "Gain" of the sensor as used in the expressions above is the inverse of FIG. 11, such that "Gain"*"Relative Gain to be Applied"=1.

In this way, the operating temperature is taken into account in the flow function Flow(t). Baseline tracking functions are described below, which also track temperature compensated functions.

After the sensor data are processed and temperature compensation is applied based on the current operating temperature, a flow-rate-dependent signal Flow(t) is produced. At this point, a simple trigger threshold check can be applied to this signal to set the approximate trigger flow rate. For the adult case, this trigger is intended to occur within the range of 0.5 LPM and 10 LPM. When a trigger is produced, the device is not actually producing a trigger at the real time flow rate; that is, it is actually producing a trigger based on the signal behavior before trigger flow rate was reached. The trigger itself is based on a combination of time delay as well as proportional and derivative combinations of both channels of sensor inputs.

By way of example, the thermistor used can have a specified resistance tolerance of ±5% at 25° C. and a tolerance of ±3% for the B value, which is a constant representing the resistance-to-temperature ratio that is dependent upon the thermistor material properties.

The intrinsic gain behavior is described above. If a given thermistor is more sensitive to temperature, it will reduce its resistance more due to a given amount of heat. Therefore, the INHALE_A voltage will be lower. Thus, a lower absolute INHALE_A voltage means the sensor is hotter and has a higher gain. Compensation is then needed with a lower gain factor.

There is also an element of gain compensation relating to the relative temperature with respect to the nominal calibration temperature.

For a given calibrated device at nominal temperature, a higher DC voltage reading corresponds to a higher thermistor resistance, and therefore represents a lower than nominal thermistor temperature. In the event of air flow, this thermistor will produce a larger signal. To equalize the gain, a lower scaling value should apply to the overall signal. Conversely, a lower DC voltage reading corresponds to a lower thermistor resistance, and therefore represents a higher than nominal thermistor temperature. In this case, in the event of air flow, this thermistor will produce a smaller signal. To equalize the gain, a higher scaling value should be applied to the overall signal. This correction is then applied to the temperature signal after temperature compensation to improve system accuracy For this purpose, a factory calibration can be performed when the inhaler is started for the first time after the firmware is loaded. Prior to the factory calibration, the inhaler temperature is for example equilibrated at 23° C.±2° C. for at least 15 minutes. At the first wakeup, the thermistor biasing is enabled, and the device goes through a warm-up period of one minute. During this period, the DC voltage of the output FLOW from the inhalation channel circuit of FIG. 5, is accumulated and averaged.

After this calibration period, the average value is stored into non-volatile flash memory and the inhaler returns to the sleep state. This value serves as the reference point for temperature compensation over the life of the device. Note that this calibration also reduces errors introduced by device-to-device variation, In particular, due to variation in thermistor resistance, different thermistors will be heated to different temperatures for a given ambient operating temperature. The DC voltage read from the inhalation channel can be used to reduce this error by applying a linear gain to the overall signal that is used for triggering.

Thus, there are two temperature compensation mechanisms. One is a real time gain compensation which is based on the real-time INHALE_A dc voltage. This gain compensation influences the parameters A, B and C. since:

$$A = Gain1 * TempGain * IntrinsicGain$$

$$B = Gain2 * TempGain * IntrinsicGain$$

$$C = Gain3 * TempGain * IntrinsicGain$$

and TempGain is the real-time gain.

The IntrinsicGain value is the second gain compensation mechanism, which set at the factory as explained above. The IntrinsicGain is a constant value that also influences the parameters A, B and C.

An A-to-D converter (ADC) is used to provide two streams of data, one from the inhalation channel circuit of FIG. 5 (combining FLOW and TEMP) and one from the flow direction amplifier of FIG. 4 (DIR signal).

A state machine is used to process this data, with a loop time is set at 6 ms; at the same time the equivalent sampling rate of the ADC is 6 ms. Each time the state machine executes, it gets one fresh data sample for each channel.

There is an initial ready mode initialization.

Each time the inhaler is awakened, it begins in a state during which a set of inhalation specific variables will be initialized and a DC baseline calibration will be initiated. The DC baseline calibration lasts for 0.5 s, during which inhalation triggering is unavailable. During this period, the user should hold the device steady to prevent the generation of unintentional flow in the flow channel.

The system makes use of baseline signals. Baseline calculation plays an important role in proper system gain compensation. The baseline is used as the reference with which the flow function Flow(t) is compared to detect an inhalation breath.

A baseline calculation is used which follows only the slowly changing waveform of the FLOW and DIR signals. During a baseline calibration period, the DC average of the FLOW signal is measured (by digital signal processing), which corresponds to the ambient temperature. This real-time temperature will be used as the starting value for the signal baseline for the duration of the current dosing session.

When there is rapid movement in the FLOW signal, the system freezes the baseline acquisition and waits for the signal to stabilize. When it does stabilize, the system captures and continues to track slow moving baseline.

The air flow proportional signal is derived from the difference between the real-time value and the baseline.

The baseline tracking involves a calibration procedure at wakeup of the device. The 0.5 second baseline calibration involves a low pass filtering of the FLOW and DIR signals with 48 ms time constant, with scaling. The scaled values are stored as baseline inhalation channel (FLOW+TEMP) and baseline DIR values.

At wakeup, the inhalation (FLOW+TEMP) and direction (DIR) channels go through a period of rapid change. Baseline calibration tracks the current values and converts them into low pass filtered values.

During normal operation, there is also baseline tracking. The transition from baseline calibration to normal operation (i.e. a state machine transition): takes place at the end of the 0.5 sec of baseline calibration. The current low pass filtered values are scaled and used as the baseline values.

Baseline or offset calculations are performed on both signals.

The baseline calculation function for the inhale channel (FLOW+TEMP) uses a fast average to track a signal with slow dynamics, and slow average to ignore signal with fast dynamics. Thus, there is tracking function which changes time constant depending on the detected signal. In doing so, a baseline TEMP signal is calculated. The TEMP signal is essentially is the DC part of the Inhale channel signal (FLOW+TEMP), but it is not a simple straight line. It follows the slow moving outline of the Inhale channel signal as the temperature of flow sensor changes.

After the baseline of the Inhale channel signal is obtained, the TEMP signal is subtracted from the Inhale channel signal for the AC signal FLOW signal to be calculated.

The FLOW signal is then is used for the Flow(t) polynomial term calculation as explained above.

The baseline calculation of the direction cannel (DIR) also uses a fast average to track a signal with slow dynamics and slow average to ignore signal with fast dynamics. Again, there is tracking function which changes time constant. In doing so, a baseline DIR signal is calculated which is essentially DC component of DIR. Again, the baseline is not a simple straight line, it follows the slow moving outline of DIR as the temperature of flow sensor changes. Due to the fact that DIR is a differential signal from two sensors, its baseline does not vary a great deal during operation of the device, due to the effect of drift cancellation.

After the baseline of DIR is obtained, the baseline is subtracted from DIR in order for the AC signal to be calculated.

The resulting AC signal is used for the Flow(t) polynomial terms calculation (as mentioned above, one term is A*DIR in which DIR is the AC part).

The temperature compensation factor is calculated from TEMP, which is used in the calculation of the values A, B and C. the Intrinsic gain is calculated from the same variable TEMP at factory calibration, and is also used in the calculation of the values A, B and C.

Thus, it can be seen that the baseline tracking involves modifying the FLOW and DIR to remove the tracked baseline, before using those signals to derive the flow function Flow(t).

In the event of flow, the baselines are disturbed. The tracking function normally uses filter with a small time constant of 48 ms for fast response when no flow is present. As soon as air flow is detected in form of significant deviation from an average value, the tracking function acts and shifts the time constant to 6.1 sec for a slow response. Eventually, air flow subsides and returns to near previous levels. When that happens, the tracking function returns to 48 ms time constant to continue with baseline fast tracking.

Figure 12:
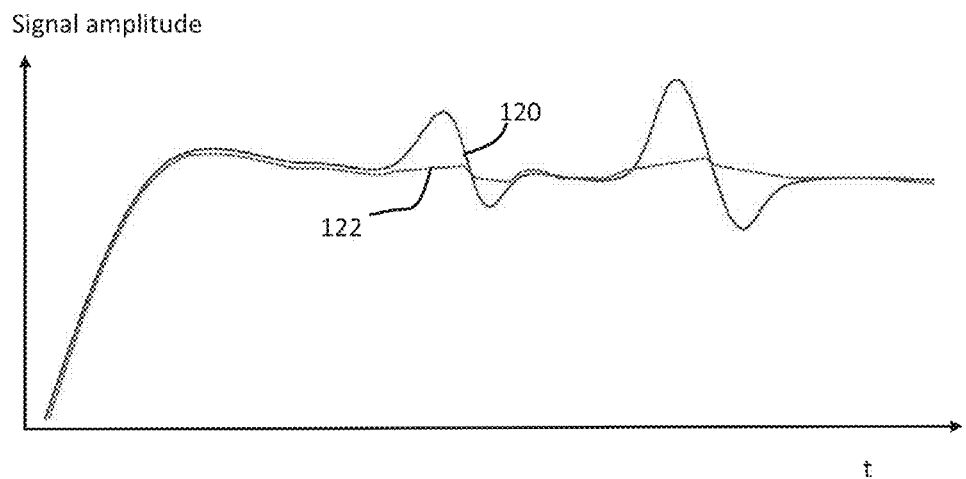
FIG. 12 is used to explain how a baseline estimator signal can be used.

This operation is shown in FIG. 12. Plot 120 can be considered to be the FLOW or DIR signals and plot 122 is a corresponding baseline function. The initial time is the power up condition, followed by two breaths.

The tracking between the baseline function and inhalation function can be seen until the function has a surge. This causes a longer time constant to be applied to the baseline function (hence a relative constant gradient as shown) until the function stabilizes again at the baseline value.

The flow function Flow(t) is used for the inhalation detection. When Flow(t) exceeds a fixed threshold level, inhalation is deterred. However, the breath needs to be screened for validation and strong exhalation. When the inhalation breath is a validated breath and it is not strong exhalation breath, a trigger is issued.

Cumulative averages are calculated in the DSP. These are used for further processing the FLOW and DIR signals, as average values over a time window are processed. Cumulative averages are also used for the baseline tracking.

For example, a first cumulative average can be defined as:

$$NewAv = \{OldAv(2^P - 1) + NewSample\}/2^P$$

This averages over a length $2^P$, with each new sample replacing one previous value. The average has a scale of 1, i.e. it has a magnitude equivalent to one sample.

A second cumulative average can be defined as:

$$NewAv = OldAv - OldAv/2^P + S$$

This average has a scale of $2^P$ i.e. it has a magnitude equivalent to $2^P$ samples. Again, one sample value is replaced with the new sample.

These cumulative calculations involve multiplying and dividing with powers of 2 which can be substituted by bitwise shift operations. These cumulative average functions can thus be computed very quickly. The second function above has fewer operations and therefore is even faster. However, it requires an average in the scale of $2^P$.

These averaging functions correspond to 1st order digital low pass filters. The time constant is determined by the value of P.

By setting different time constants, i.e. values of P, the baseline tracking can be applied with different time constant, based on the detection of an inhalation.

The following functions are executed to process the sensor signals that are updated every 6 ms:

(i) Update long-term averages of both the inhalation (FLOW+TEMP) and direction (DIR) signals.

(ii) Update the ambient temperature-dependent DC offset value (TEMP). This value is updated in real-time so that ambient temperature is estimated in real-time. During the course of inhalation, the ambient+sensor combination signal tends to drift. This variable tracks the drift so that it can be corrected.

(iii) Store an inhalation signal baseline estimation value.

The real time flow calculation involves defining a polynomial function Flow(t), as explained above.

The software to carry out the control is based on a software state machine. The operating states are defined as follows:

Inhalation_State_Calibrating:

This state determines if the device wakeup is the first wakeup after initialization. If so, the factory temperature baseline calibration is performed. The calibration result is stored in flash memory, then the inhaler enters the sleep state.

Inhalation_State_Calibrated:

The factory temperature baseline calibration is complete.

Inhalation_State_Initialize_Baseline:

At the beginning of every dosing session immediately following wake-up, the baseline correlating to operating temperature is established. When the inhaler device is awakened any time after the first time, the state machine will default to begin in this state. It will initialize the inhalation related variables, including the long-term averages.

Inhalation_State_Blanking:

This is a delay period to reduce the chance of the signal from the previous breath corrupting the detection attempt of the subsequent breath. This period, begins at the start of breath detection. A value of 600 ms is currently used for the blanking period. During this period, the device is waiting for the analog channels to stabilize before the next breath detection. After which, state machine will return to INHALATION_STATE_DETECT (below).

Inhalation_State_Detect:

In this state, the inhalation signal prim-egging takes plane, and the resultant signal is compared against a baseline threshold to generate a trigger.

Because of the high sensitivity of the inhalation detection system, rapid movement of the inhaler, especially with an adult facemask attached, can cause air to flow through the flow channel and can result in unwanted triggers. There is therefore breathing validation to reject motion-induced triggers. While there are various methods for eliminating false triggers due to device motion (for example, using a low-cost accelerometer to provide device motion information, a "dead man" switch actuated by the user when the inhaler is in place, sensing of the inhaler's proximity to the user's face, a spring-loaded valve that closes off the inhaler's flow channel when not pressed against the user's face, to name a few), the current embodiment uses a software filtering scheme.

The software filter operates under the assumption that a minimum of three consecutive breaths with relatively regular intervals indicate a tidal breathing condition. It is only after this condition is met that triggering of drug delivery begins, and the breathing intervals must remain relatively constant in order for dosing to continue. As a result, the filter will reject spurious inhalation signals due to device handling, which are more likely to occur before dosing begins while the inhaler is being positioned on the user's face. Once tidal breathing has been established, the operation of the software filter is essentially transparent to the user.

Figure 17:
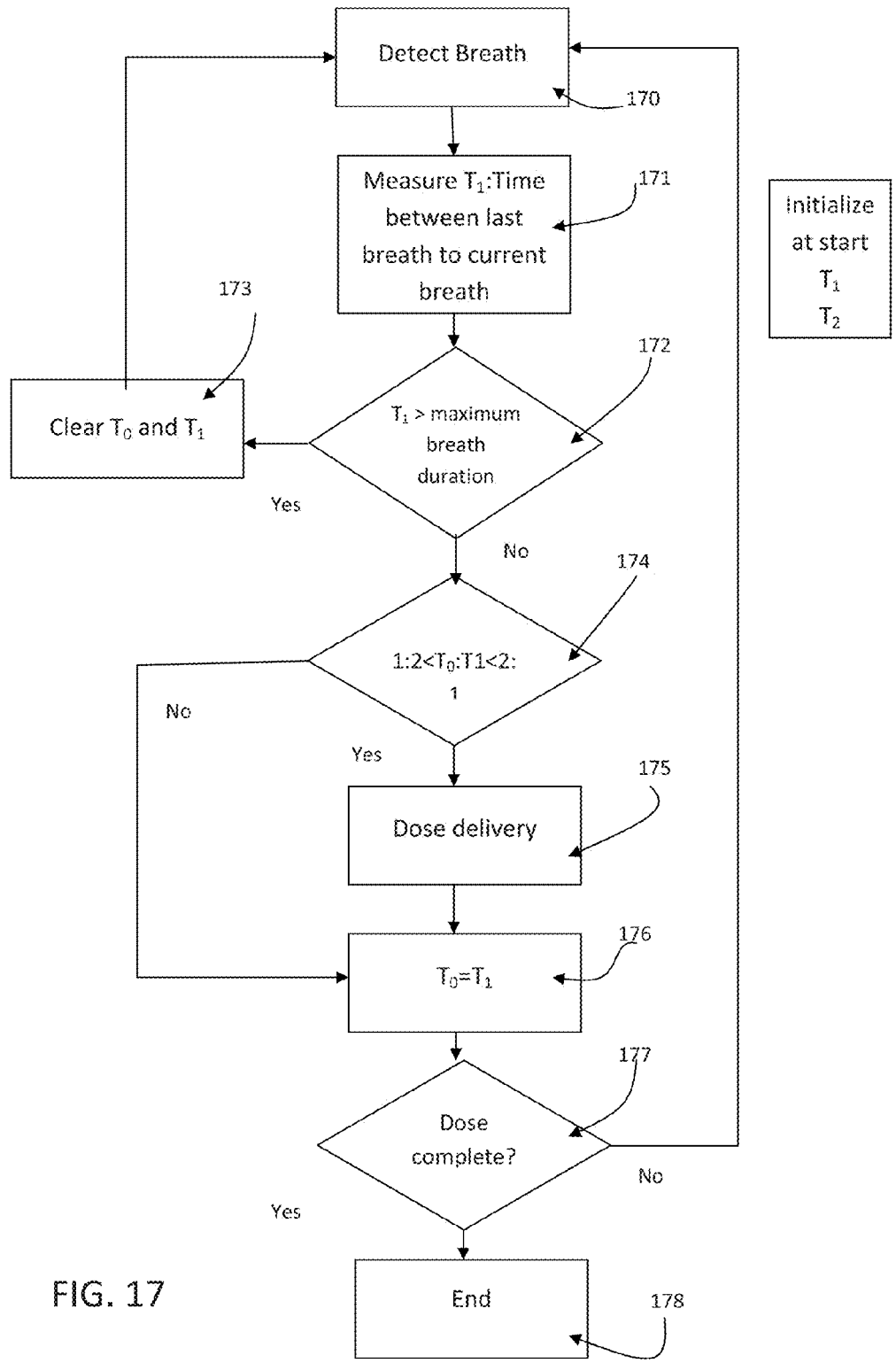
FIG. 17 is a second flow chart to illustrate the method of the invention in controlling the dose bursts.

In summary, the software filter operates as follows, and a more complete description is given below with reference to FIG. 17:

Following the first valid inhalation detection after the inhaler is started, elapsed time is measured until the next valid inhalation is detected. This first interval, is stored as $T_0$.

The time between the second valid inhalation and the third valid inhalation is also measured, stored as $T_1$.

Immediately after detecting the third valid inhalation, the intervals $T_1$ and $T_1$ are compared. If the ratio of the intervals falls into the range of 1:2 to 2:1, the inhalations are assumed to be "regular", and a trigger is issued by the microcontroller to deliver the first dosing burst.

The current value of $T_1$ is stored into $T_1$.

When the next valid inhalation is detected, a new value of $T_1$ is computed, and the two intervals are compared again. As long as the ratio between the two intervals remains within the range of 1:2 to 2:1, new triggers are issued when inhalations are detected.

If two consecutive intervals do not satisfy the desired ratio range, OR if the most recent interval exceeds a predetermined upper limit, dosing is suspended, the software filter is reset, and dosing cannot resume until three consecutive breaths having intervals within the desired range are again detected.

This breathing validation process continues, looking only at the two most recent inhalations at any given point in time, until the dose is complete or a dosing timeout occurs. Since only the two most recent inhalation intervals are used, the algorithm is able to adapt to slower changes in breathing frequency throughout the dosing session.

The processing based on three or more consecutive breaths also assists in the rejection of motion-induced triggers. The assumption is that a minimum of three consecutive breaths with relatively regular intervals indicates a tidal breathing condition. It is only after this condition is met that triggering of drug delivery begins, and the breathing intervals must remain relatively constant in order for dosing to continue. As a result, the filter will reject spurious inhalation signals due to device handling, which are more likely to occur before dosing begins while the inhaler is being positioned on the user's face. Once tidal breathing has been established, the operation of the software filter is essentially transparent to the user.

Figure 13:
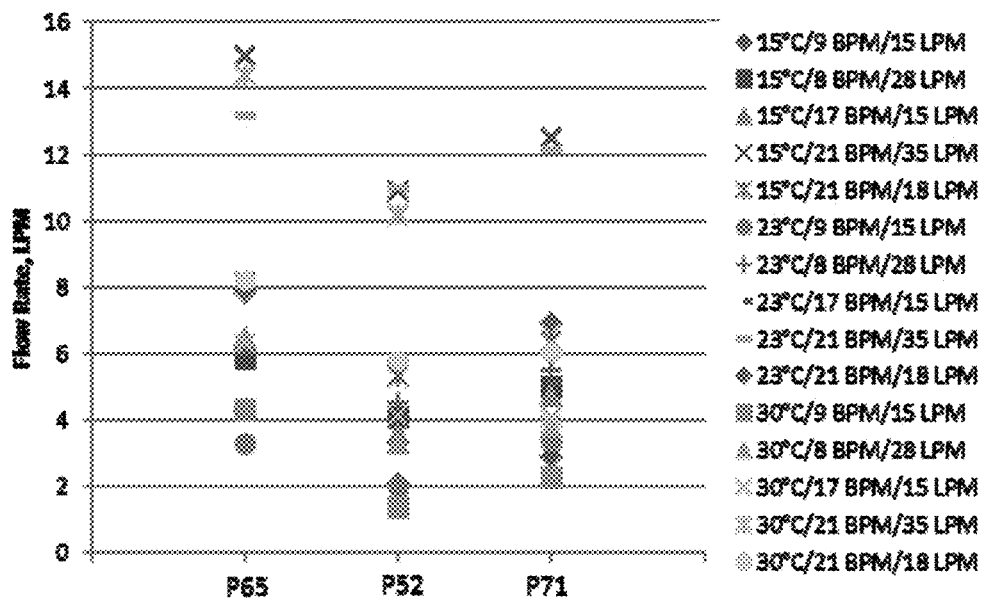
FIG. 13 shows the flow rate at the trigger point (i.e. when the vibrating element is actuated to release the dose) for a range of operating temperatures, flow rates and breathing rates.

FIG. 13 shows flow rates at the trigger point (each point averaged across 16 inhalations) across a range of sinusoidal flow profiles and operating temperatures for three inhalers.

The key indicates the temperature, number of breaths per minute (BPM) and flow rate (LPM). This figure shows that for the range of possible operating conditions, the flow rate at which the dose is triggered remains within desired boundaries, with a lower trigger point at lower flow rates.

Figure 14:
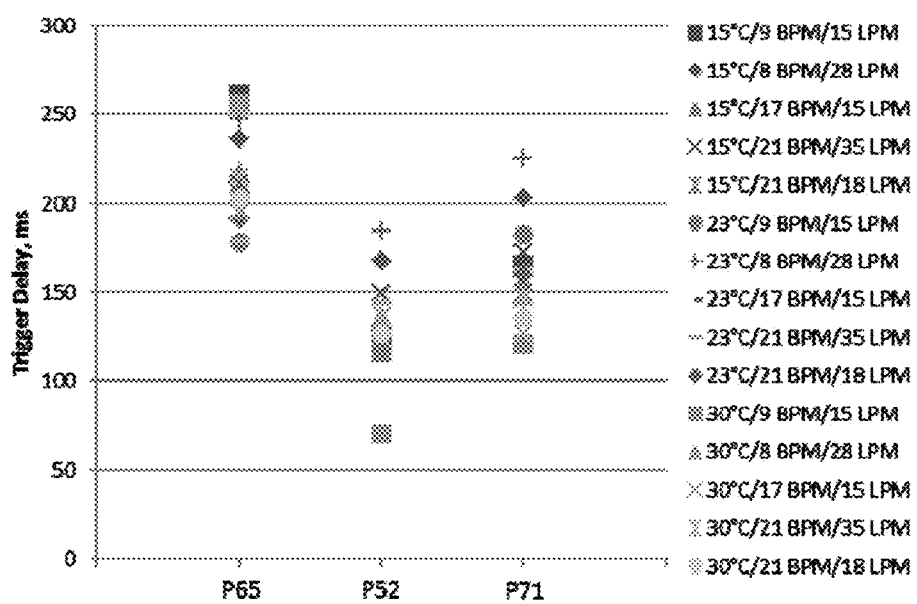
FIG. 14 shows the trigger delay point for a range of operating temperatures, flow rates and breathing rates.

FIG. 14 shows the trigger delays measured from the point in time at which the flow rate has reached 0.5 LPM (each point averaged across 16 inhalations) across a range of sinusoidal flow profiles and operating temperatures for three inhalers. Again, the trigger delay remains in acceptable bounds.

FIGS. 13 and 14 show that when presented with a variety of sinusoidal flow patterns ranging from 8 to 21 breaths/min and tidal volumes of 300 to 1100 mL during characterization studies, the trigger point varies over a range of 0.8 LPM to 15.5 LPM (average=5.8 LPM) with a delay ranging from 24.5 ms to 297 ms (average=159 ms) as measured after the inspiratory flow rate reaches 0.5 LPM.

Figure 15:
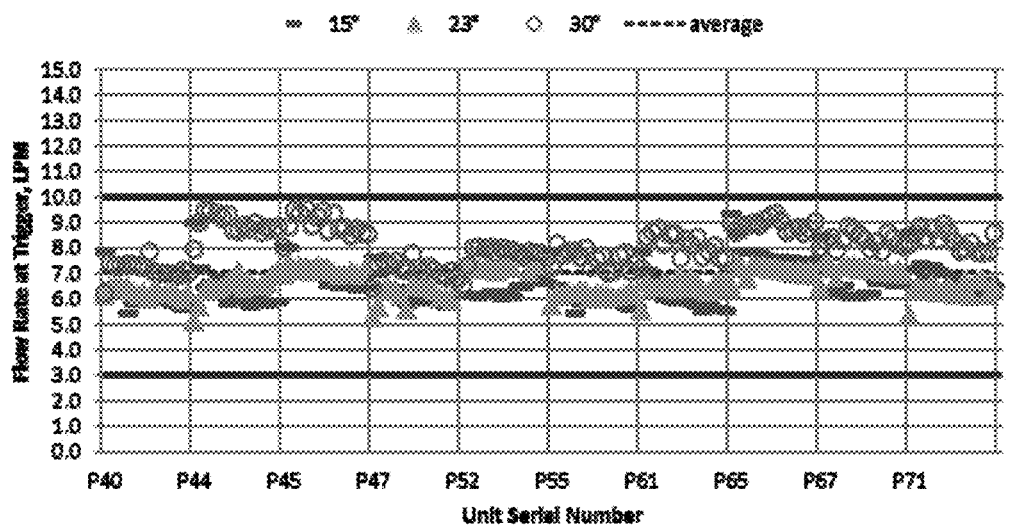
FIG. 15 shows the trigger flow rates for different temperatures.

FIG. 15 shows the performance of the inhalation detection system across 10 different inhalers tested at 15° C., 23° C. and 39° C. using the European adult standard breathing profile of a 15 LPM peak sinusoidal waveform with an inhalation-to-exhalation ratio of 1:1 and a tidal volume of 500 mL. All devices triggered within a 3 to 10 LPM range over the operating temperature range. The solid lines at 3 and 10 LPM represent target detection limits.

Accuracy of the trigger point depends on the air flow ramp rate. Based on signal processing response times, sharp increases in air flow tend to result in triggering at a higher flow rate.

Due to very high sensitivity to low flow rates, motion of the inhaler can result in air flow through the flow channel—an effect that is amplified with a face mask installed—which can be interpreted as valid inhalation by the detection algorithm. The inhalation detection algorithm includes a method for rejecting spurious flow signals assumed to be from inhaler motion.

There can be differences between adult and pediatric applications.

The pediatric mask typically consists of a shallow silicone cup with a single port that channels both inhalation and exhalation through the device. The larger adult mask can have a separate exhalation vent port such that only inhalation passes through the flow channel, whereas exhalation flow through the device is significantly attenuated. Substantial exhalation air flow will occur in the flow channel only with very strong exhalation flow.

The algorithm can tolerate both types of mask.

However, if desired, different detection algorithms for the different mask types. Possible differences between the adult and pediatric detection algorithms are described below:

Adult Case:

Amplitude detection applies an estimated baseline to the current signal amplitude to represent the flow signal.

Exhalation trigger rejection: there is less need for trigger rejection for exhalation due to the fact that there is no significant flow in the flow channel during exhalation. This is particularly the case if the adult is using a large mask with vent port. In this case, exhalation in the flow channel will be minimal, so the direction signal contains very little exhalation information. Therefore, the estimated baseline value can be subtracted from the real-time direction signal.

Pediatric Case:

Amplitude detection first has to detect the inhalation and the exhalation phases of the flow signal, then only the inhalation phase of the amplitude is used for inhalation representation.

Exhalation trigger rejection: a trigger rejection algorithm must be used to reject exhalation. This is particularly challenging when pediatric patient is capable of producing strong exhalation air flow while coughing or sneezing. Sometimes, those strong exhalations are stronger than the strongest inhalation. A more sophisticated algorithm has been designed to overcome this challenge. For example, for the device to trigger, the system can require both inhalation channels (FLOW and DIR) to be positive going. If a violation occurs during a significant FLOW condition, the system can disable triggering. When such a violation occurs, an extended triggering blackout period can block out triggering until the strong exhalation subsides.

For example, before a change in DIR signal from inhalation to exhalation, i.e. shortly after the DIR signal has reached a maxima, the derivative will be close to zero. At this point, a blocking window, for example of 300 ms, can be established. Inhalation cannot have started within 300 ms of switching from inhalation to exhalation, so that any trigger in this period is a false trigger.

There are various calibration requirements which have been discussed above.

As explained above, a reference temperature is measured at initial factory calibration under a controlled temperature environment and stored in Flash memory in the Power-On Self-Test (POST) state. After applying power, the temperature calibration can be performed as follows:

Ensure that the device is at an ambient temperature of 23° C.±2° C.;

Enable the 3.6 V power supply;

Sample the FLOW signal at the sample rate to be used during inhalation monitoring;

Average the signal over one minute; and

Store the average signal in flash memory as the reference baseline value.

The invention makes use of a controller to implement the processing of signals and generation of the control signals for the vibrator element and drive mechanism. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller.

In the examples above, the measured flow sensor signals are processed by amplifier circuitry to derive the direction (DIR), flow (FLOW), temperature (TEMP) and derivative signals. These circuits can be considered to be part of the overall controller, of which the processor 26 then only forms a part. However, the flow sensor signals can instead by sampled by A/D converters, and then all processing can be carried out in software. Thus, the different functions required to derive the flow function can be divided differently between hardware and software. For example, analogue circuitry can be used to bias the thermistors, and to provide signal gain, but the remaining processing can be carried out by a DSP.

Figure 16:
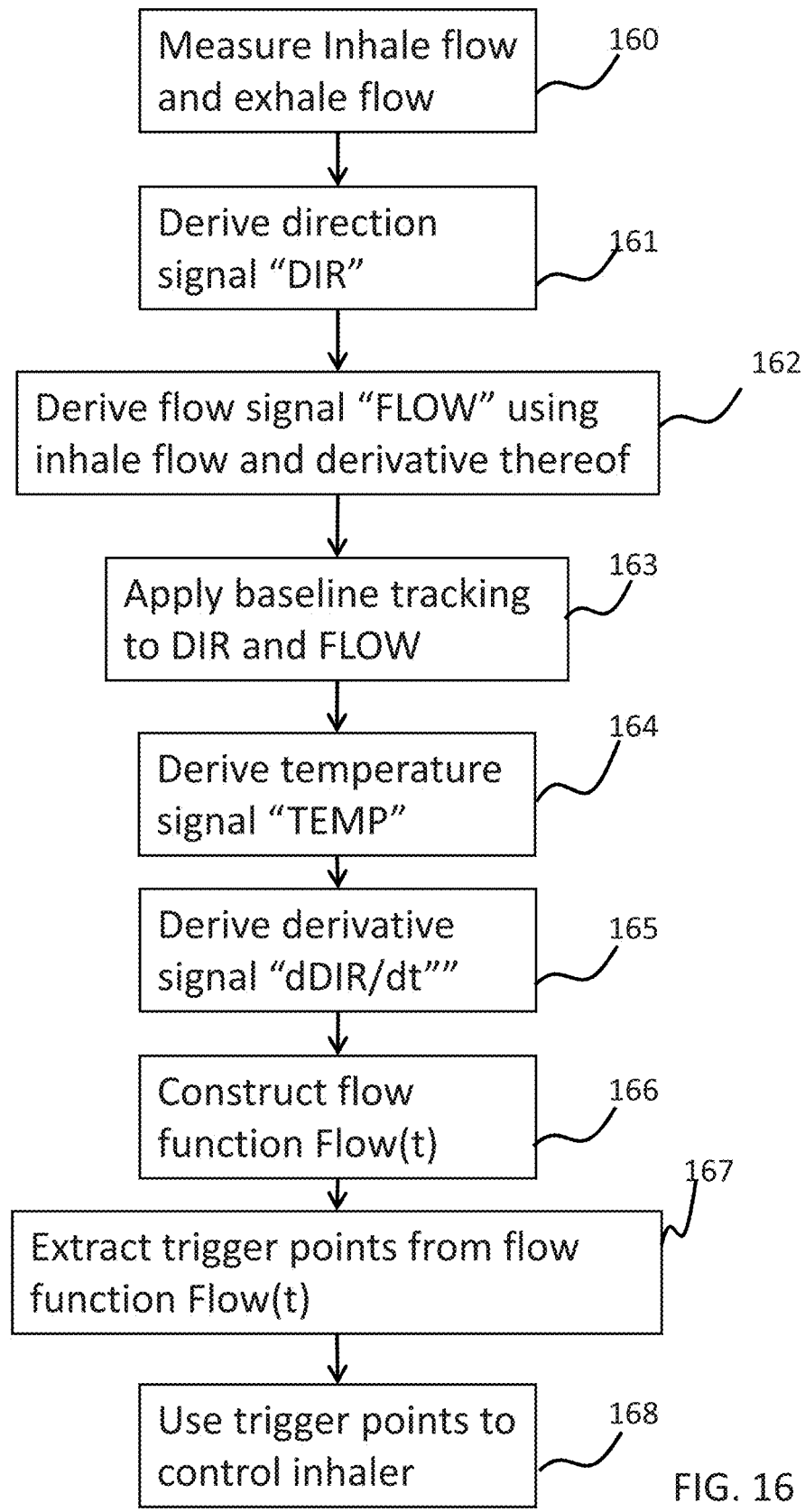
FIG. 16 is a first flow chart to illustrate the method of the invention in forming the flow function.

FIG. 16 shows generally the method for constructing the flow function and then extracting trigger timing points (after the baseline calibration is complete). In step 160, the inhale and exhale flows are measured by the sensors. The direction signal "DIR" is obtained (step 161) from the difference between the flow sensor signal, and the flow signal "FLOW" is obtained (step 162) from the inhale sensor alone.

Baseline tracking is used to remove the baseline components in step 163, so that baseline-compensated (AC parts) of the DIR and FLOW signals are obtained for use in forming the flow function Flow(t).

The ambient temperature indication "TEMP" is obtained as the DC component of the FLOW signal (step 164).

The derivative of the baseline-compensated direction signal is obtained in step 165.

The polynomial flow function can then be constructed in step 166.

The flow function is used to extract trigger points representing inhalation time points (step 167) and these are used to control drug delivery, in particular by controlling the vibratory element and dose advance mechanism (step 168).

As explained above, the use of the trigger points is controlled to avoid false delivery. FIG. 17 shows the process employed, as explained above.

At the start, two timing values T0 and T1 are reset.

In step 170, a breath inhalation is detected, by comparing the flow function value with the baseline function.

In step 171 the time T1 since the last breath is measured. If this time is longer than a threshold, as determined in step 172 (because it is the first breath measured), the timing values are reset in step 173 and the next breath is awaited.

When the next breath is detected, the time T1 since the last breath is within the threshold.

As a result, the process proceeds to step 174. Note that T0 still has a reset value at this time.

The two preceding time intervals are compared in step 174 to see if they are within the acceptable range of 2:1 to 1:2 and that the last delay is not too long.

If they meet the criteria, there is a dose delivery in step 175.

For the second breath, the criteria is not met, since T0 is still reset.

The time intervals are shifted along by one in step 176, so that present $T_1$ replaces $T_0$.

If dosing is not complete (step 177) the next inhale is detected hack in step 170. If dosing is complete, the cycle ends (step 178).

Only when measuring the third breath will the condition in step 174 first be satisfied, since this time both T0 and T1 have values which represent normal time periods between breaths.

If the breathing pattern was not regular as determined in step 174, then the current value of T1 is either too large or too small and no dose is delivered. T1 is then set to T0 anyway, and the next breath is awaited, so that T1 can be captured and compared to T0.

Figure 18:
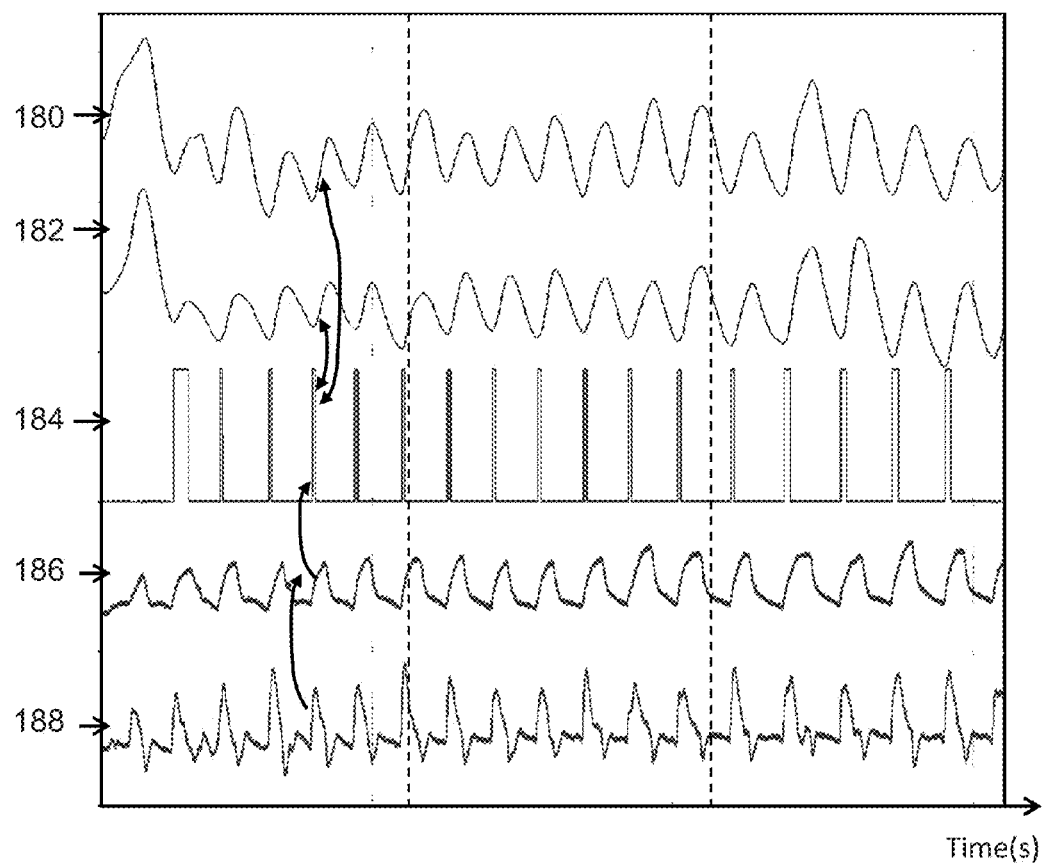
FIG. 18 shows the relationship between different signals used by the system, including the FLOW and DIR signals, and additionally the TRIGGER signal.

FIG. 18 shows the relationship between different signals used in the system, including the FLOW and DIR signals as shown in the plots above, but additionally the TRIGGER signal. FIG. 18 shows the operation over a greater number of breaths than the plots of FIGS. 7 to 10.

Plot 180 shows the output of a respiratory inductance plethysmography (RIP) belt around the thorax and plot 182 shows the output of an RIP belt around the abdomen. These provide independent breathing measures to enable the correct operation of the system to be shown. The rising signal in each of these plots indicates the start of expansion of the chest/abdomen, i.e. inhalation.

Plot 184 shows the TRIGGER signal, plot 186 shows the DIR signal and plot 188 shows the FLOW signal. The sharp rising edge of the FLOW signal 188 indicates inhalation flow, and the peak amplitude is proportional to the initial respiratory flow rate. A rising edge of the DIR signal 186 indicates inspiratory flow and the falling signal indicates expiratory flow.

The TRIGGER events occur during rising edges of both DIR and FLOW signals, as represented by arrows in FIG. 18.

FIG. 18 shows that the trigger events coincide with the beginning of RIP belt movement as inhalation starts.

The first trigger event initiates blister advance, exposing the drug to the dosing chamber, before dosing starts. With each of the remaining 16 triggers, a portion of the medication is released into the flow channel by the electrically driven vibratory element. The full sequence of 17 trigger pulses (one per inhalation) corresponds to delivery of one dose capsule. The trigger pulses then cease until the next dose is initiated. Note that the first trigger pulse width appears longer only because of the simulation used (it is simulating the time that it takes to execute a dose advance).

To give an idea of scale, the dotted vertical lines are separated by a time period of 10 seconds.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

We claim:

1. An inhalation device for delivering medication from a container through a flow channel to a patient, said inhalation device comprising:
   an electrically driven vibratory element;
   a blister pack advancement mechanism;
   a controller configured to activate the vibratory element; and
   a sensor arrangement system configured to generate signals indicative of inhalation,
   wherein the controller is configured to process the signals indicative of inhalation, determine that a first inhalation flow signal of a first inhalation is above a threshold and generate a first trigger signal for advancing the blister pack advancement mechanism based on the first inhalation flow signal being above the threshold, and determine that a second inhalation flow signal of a second inhalation is above the threshold and generate a second trigger signal for controlling a timing of operation of the vibratory element for releasing medication into the flow channel based on the second inhalation flow signal being above the threshold.

2. An inhalation device as claimed in claim 1, wherein the controller is configured to, after the controller transitioning from a sleep state to an on state, generate the first trigger signal for advancing the blister advancement mechanism based on the first inhalation flow signal being above the threshold.

3. The inhalation device as claimed in claim 1, wherein the sensor arrangement system comprises a first sensor physically arranged to face inhalation air and a second sensor physically arranged to face exhalation air, and wherein the first sensor and the second sensor each comprise thermistor sensors.

4. The inhalation device as claimed in claim 1, wherein the controller is configured to determine that a preliminary inhalation flow signal is above the threshold, and wherein the preliminary inhalation flow signal is determined prior to the first inhalation flow signal, and the first inhalation flow signal is determined prior to the second inhalation flow signal.

5. The inhalation device as claimed in claim 4, wherein the preliminary inhalation flow signal, the first inhalation flow signal, and the second inhalation flow signal are determined based on consecutive inhalations.

6. The inhalation device as claimed in claim 1, wherein the controller is configured to determine the first inhalation flow signal from a first signal indicative of inhalation from the sensor arrangement system, and determine the second inhalation flow signal from a second signal indicative of inhalation from the sensor arrangement system.

7. The inhalation device as claimed in claim 1, wherein the controller is configured to generate the second trigger signal only after a plurality of consecutive inhalation flow signals are determined to be above the threshold.

8. The inhalation device as claimed in claim 1, wherein the controller is configured to determine that an intermediate inhalation flow signal is below the threshold and suspend a dosing procedure based on the intermediate inhalation flow signal being below the threshold.

9. The inhalation device as claimed in claim 1, wherein the controller is configured to generate the second trigger signal for controlling the timing of operation of the vibratory element based on the second inhalation flow signal being above the threshold and subsequent to generating the first trigger signal.

10. The inhalation device as claimed in claim 1, wherein the vibratory element comprises a piezo electric vibrator.

11. A method of controlling an inhalation device for delivering medication from a container through a flow channel to a patient, the method comprising:
receiving signals indicative of inhalation from a sensor arrangement system;
determining that a first inhalation flow signal of a first inhalation is above a threshold;
generating a first trigger signal for advancing a blister pack advancement mechanism based on the first inhalation flow signal being above the threshold;
determining that a second inhalation flow signal of a second inhalation is above the threshold;
generating a second trigger signal for controlling a timing of operation of an electrically driven vibratory element for releasing the medication into the flow channel based on the second inhalation flow signal being above the threshold.

12. A method as claimed in claim 11, further comprising determining the first inhalation flow signal from a first signal indicative of inhalation from the sensor arrangement system, and determining the second inhalation flow signal from a second signal indicative of inhalation from the sensor arrangement system.

13. A method as claimed in claim 11, further comprising, after the controller transitions from a sleep state to an on state, generating the first trigger signal for advancing the blister pack advancement mechanism based on the first inhalation flow signal being above the threshold.

14. A method as claimed in claim 11, further comprising determining that a preliminary inhalation flow signal is above the threshold, and wherein the preliminary inhalation flow signal is determined prior to the first inhalation flow signal, and the first inhalation flow signal is determined prior to the second inhalation flow signal.

15. A method as claimed in claim 14, wherein the preliminary inhalation flow signal, the first inhalation flow signal, and the second inhalation flow signal are determined based on consecutive inhalations.

16. A method as claimed in claim 11, further comprising generating the second trigger signal only after a plurality of consecutive inhalation flow signals are determined to be above the threshold.

17. The method of claim 11, further comprising determining that an intermediate inhalation flow signal is below the threshold, and suspending a dosing procedure based on the intermediate inhalation flow signal being below the threshold.

18. The method of claim 11, wherein the sensor arrangement system comprises a first sensor physically arranged to face inhalation air and a second sensor physically arranged to face exhalation air, and wherein the first sensor and the second sensor each comprise thermistor sensors.

19. The method of claim 11, further comprising generating the second trigger signal for controlling the timing of operation of the vibratory element based on the second inhalation flow signal being above the threshold and subsequent to generating the first trigger signal.

20. The method of claim 11, wherein the vibratory element comprises a piezo electric vibrator.

* * * * *